(12) United States Patent
Matsushita (10) Patent No.: US 10,509,010 B2
(45) Date of Patent: Dec. 17, 2019

(54) VACUUM PROCESSING APPARATUS AND MASS SPECTROMETER

(71) Applicant: SHIMADZU CORPORATION, Kyoto-shi, Kyoto (JP)

(72) Inventor: Tomoyoshi Matsushita, Manchester (GB)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/777,352

(22) PCT Filed: Nov. 20, 2015

(86) PCT No.: PCT/JP2015/082743
§ 371 (c)(1),
(2) Date: Oct. 22, 2018

(87) PCT Pub. No.: WO2017/085874
PCT Pub. Date: May 26, 2017

(65) Prior Publication Data
US 2019/0033256 A1 Jan. 31, 2019

(51) Int. Cl.
*G01N 27/62* (2006.01)
*H01J 49/04* (2006.01)
(Continued)

(52) U.S. Cl.
CPC .......... *G01N 27/622* (2013.01); *G01N 27/62* (2013.01); *H01J 49/04* (2013.01); *H01J 49/0418* (2013.01);
(Continued)

(58) Field of Classification Search
None
See application file for complete search history.

(56) References Cited

U.S. PATENT DOCUMENTS 4,949,671 A * 8/1990 Davis .................. H01J 37/3244
118/715
4,988,533 A * 1/1991 Freeman ............... C23C 16/402
427/294
(Continued)

FOREIGN PATENT DOCUMENTS

JP 03-288429 A 12/1991
JP 03288429 A * 12/1991
(Continued)

OTHER PUBLICATIONS

Written Opinion of the International Searching Authority of PCT/JP2015/082743 dated Dec. 22, 2015.
(Continued)

*Primary Examiner* — Andrew Smyth
(74) *Attorney, Agent, or Firm* — Sughrue Mion, PLLC (57) ABSTRACT

A vacuum processing apparatus 1 includes a processing chamber 3 that can bring an inside of the processing chamber into a vacuum state, a load lock chamber 2 that is coupled to the processing chamber 3 and that is switchable between an atmospheric state and the vacuum state, a communication unit 10 configured to communicate the processing chamber 3 and the load lock chamber 2, a stage 5 on which a processing object 9 is placed, the stage being movable between the processing chamber 3 and the load lock chamber 2 through the communication unit 10, and a sealing unit 6 fixed to the stage 5, the sealing unit being larger than an opening 300 of the communication unit 10 on a side of the processing chamber 3.

5 Claims, 7 Drawing Sheets

(51) Int. Cl.
*H01J 49/14* (2006.01)
*H01J 49/16* (2006.01)
*H01J 49/24* (2006.01)

(52) U.S. Cl.
CPC .......... *H01J 49/0495* (2013.01); *H01J 49/14* (2013.01); *H01J 49/164* (2013.01); *H01J 49/24* (2013.01)

(56) References Cited

U.S. PATENT DOCUMENTS

| | | | | |
|---|---|---|---|---|
| 5,138,973 A | * | 8/1992 | Davis | C23C 16/482 118/719 |
| 5,248,636 A | * | 9/1993 | Davis | C23C 16/482 216/63 |
| 5,340,261 A | * | 8/1994 | Oosawa | H01L 21/67745 118/719 |
| 8,872,103 B2 | * | 10/2014 | Holle | H01J 49/0004 250/282 |
| 2003/0161706 A1 | * | 8/2003 | Kurita | H01L 21/68 414/217 |
| 2006/0182532 A1 | * | 8/2006 | Okada | H01L 21/67201 414/217 |
| 2012/0195717 A1 | * | 8/2012 | Krupyshev | H01L 21/67126 414/217 |

FOREIGN PATENT DOCUMENTS

| | | |
|---|---|---|
| JP | 2012-015331 A | 1/2012 |
| JP | 2012015331 A * | 1/2012 |

OTHER PUBLICATIONS

International Search Report of PCT/JP2015/082743 dated Dec. 22, 2015.

* cited by examiner

VACUUM PROCESSING APPARATUS AND MASS SPECTROMETER

CROSS REFERENCE TO RELATED APPLICATIONS

This application is a National Stage of International Application No. PCT/JP2015/082743 filed Nov. 20, 2015.

TECHNICAL FIELD

The present invention relates to a vacuum processing apparatus that processes an object under vacuum. For example, the present invention relates to a mass spectrometer that performs mass spectrometry of a sample under vacuum.

BACKGROUND ART

For example, a mass spectrometer, which ionizes a sample by irradiating the sample with a laser beam under vacuum, accelerates the ions to fly, and separates and detects the flying ions according to their mass-to-charge ratio, is known as a vacuum processing apparatus that processes an object wider vacuum (for example, Patent Literature 1).

In this type of apparatus, for example, a door between a processing chamber and the outside of the apparatus is opened to bring an object in the processing chamber, the door is closed to evacuate the processing chamber, and the object is processed. When the process is ended, the vacuum in the processing chamber is broken, and the door is opened to bring the object out of the processing chamber. However, in this manner, if the vacuum in the processing chamber is broken and the evacuation is performed each time the object is exchanged, it takes much time to replace objects in the processing chamber, and the throughput of the apparatus is very low.

For this reason, sometimes a load lock chamber is provided between the processing chamber and the outside of the apparatus (for example, Patent Literature 2). In the apparatus of Patent Literature 2, a door (first door) separating the outside of the apparatus from the load lock chamber is opened, the object s brought in the load lock chamber, and the load lock chamber is evacuated. When the load lock chamber reaches a preset degree of vacuum, another door (second door) separating the load lock chamber from the processing chamber (which is maintained at the preset degree of vacuum) is opened. Specifically, the second door is constructed with a gate valve. When the second door is opened, a transfer robot disposed in the processing chamber extends an extensible arm to enter a hand to the load lock chamber, grips the object in the load lock chamber, shrinks the arm to return the hand to the processing chamber, and transfers the object to the processing chamber. When the arm retreats from the load lock chamber, the second door is closed and the object is processed in the processing chamber. When the process on the object is ended, the second door is opened. The transfer robot grips the processed object existing in the processing chamber with the hand, advances the hand into the load lock chamber to transfer the object to the load lock chamber, and places the object at a predetermined position in the load lock chamber. Then, after the arm of the transfer robot retreats from the load lock chamber, the second door is closed. When the second door is closed to separate the processing chamber and the load lock chamber, the load lock chamber is opened to the atmosphere, and the object is brought out from the apparatus.

Normally, the size of the load lock chamber is made minimum for exchanging the object with the outside of the apparatus. Thus, the internal volume of the load lock chamber is smaller than the internal volume of the processing chamber in which the equipment or the like necessary for process is disposed. When the load lock chamber is provided in the apparatus, it is only necessary, in exchanging the object, to evacuate the load lock chamber alone which has relatively smaller internal volume, and the necessity of evacuating the processing chamber having a relatively lamer internal volume is reduced.

CITATION LIST

Patent Literature

Patent Literature 1: U.S. Pat. No. 5,872,103
Patent Literature 2: JP 2012-015331 A

SUMMARY OF INVENTION

Technical Problem

When the load lock chamber is provided in the apparatus, the following disadvantage arises while the above advantage is obtained. In the case that the load lock chamber is not provided, the operation to transfer the object between the outside of the apparatus and the processing chamber is enough, but in the case that the load lock chamber is provided, it is necessary to perform operations: to transfer the object between the outside of the apparatus and the load lock chamber; to transfer the object between the load lock chamber and the processing chamber; and to separate the load lock chamber from the processing chamber (these operations are hereinafter simply referred to as an exchange operation). For example, in Patent Literature 2, as described above, the exchange operation is performed by such a series of operations that the second door is opened, the transfer robot advances the hand gripping the processed object into the load lock chamber and transfers the object to the load lock chamber, and the second door is closed after the arm of the transfer robot retreats from the load lock chamber. In this case, time necessary for the exchange operation is a sum of a movement time of the arm and an opening and closing time of the door.

A problem to be solved by the present invention is to provide a technique capable of suppressing the time necessary for the exchange operation between the load lock chamber and the processing chamber in a short time in the apparatus configuration including the load lock chamber.

Solution to Problem

According to one aspect of the present invention, a vacuum processing apparatus includes: a processing chamber that can bring an inside of the processing chamber into a vacuum state; a load lock chamber that is coupled to the processing chamber and that is switchable between an atmospheric state and the vacuum state; a communication unit configured to communicate the processing chamber with the load lock chamber; a stage on which a processing object is placed, the stage being movable between the processing chamber and the load lock chamber through the communication unit; and a sealing unit fixed to the stage, the sealing unit being larger than an opening of the communication unit on a processing chamber side.

Before processing, the processing object is brought from the outside into the load lock chamber, and placed on the stage while the stage is located on the load lock chamber side. At this point, the opening of the communication unit on the processing chamber side is sealed by the sealing unit fixed to the stage. Thus, the processing chamber is not open to the atmosphere. After the load lock chamber is switched from the atmospheric state to the vacuum state, the stage on which the object is placed is moved from the load lock chamber to the processing chamber, and the object is transferred to the processing chamber. Then, the process on the object placed on the stage is performed under vacuum in the processing chamber. When the process is ended in the processing chamber, the stage on which the processed object is placed is moved from the processing chamber to the load lock chamber side, and the object is transferred to the load lock chamber. When the stage is disposed on the load lock chamber side, the opening of the communication unit on the processing chamber side is sealed by the sealing unit again. At this point, the load lock chamber is opened to the atmosphere, and the object on the stage is brought out to the outside of the apparatus.

In this way, in this aspect, the position of the stage interlocks with the closing and opening of the communication unit, and the load lock chamber and the processing chamber are naturally separated from each other when the object is transferred from the processing chamber to the load lock chamber. Thus, the time necessary for the exchange operation between the load lock chamber and the processing chamber can be shortened.

Additionally, in this aspect, the closing and opening operation of the communication unit interlocks with the moving operation of the object, so that the number of components of the apparatus can be decreased, which reduces the manufacturing cost of the apparatus.

Additionally, in this aspect, the configuration that closes and opens the communication unit can be simplified, so that the volume of the load lock chamber can be kept small. Consequently, the time necessary for the evacuation of the load lock chamber can be shortened (for example, several seconds).

Preferably, the vacuum processing apparatus includes: a plate-shaped member rotatable provided on a horizontal axis placed above the opening of the communication unit on the processing chamber side in an inner wall of the processing chamber, the plate-shaped member being switchable between a closed state in which the plate-shaped member abuts on the inner wall and an opened state in which the plate-shaped member is detached from the inner wall; and a penetration opening formed in the plate-shaped member to allow the stage to pass. An opening end of the penetration opening on the inner wall side is formed at a position corresponding to the opening of the communication unit on the processing chamber side when the plate-shaped member is in the closed state, while the penetration opening is inclined obliquely downward as the penetration opening goes away from the inner wall, an inclined portion inclined obliquely downward at an angle equal to that of the penetration opening is formed at an end of the stage on a side on which the sealing unit is fixed as it approaches the sealing unit, the sealing unit is larger than an opening end of the penetration opening on a side opposite to the inner wall, and in a state in which the stage is located on a load lock chamber side, the inclined portion of the stage is disposed inside the penetration opening, and the sealing unit abuts on the plate-shaped member to bring the plate-shaped member into the closed state.

In this aspect, the opening on the processing chamber side of the communication unit is sealed by the sealing unit with the plate-shaped member interposed between them while the stage is located on the load lock chamber side. At this point, the penetration opening of the plate-shaped member is obliquely formed, and corresponding to this, the inclined portion is formed at the base end of the stage. For this reason, the position of the sealing unit with respect to the top surface of the stage can be lowered by the inclination of the inclined portion. According to this aspect, even if some sort of component or the like is disposed close to the top surface of the stage due to a layout of the processing chamber, interference between the component and the sealing unit can be avoided.

For example, in the mass spectrometer that is a kind of the vacuum processing apparatus, an electrode ("an extraction electrode") that extracts a substance ionized by irradiating the object (sample) on the stage with a laser beam is provided at a position very close to the object on the stage (for example, the position at which a separation distance from the object is about 3 mm). In this case, if a portion projecting higher than the top surface of the stage exists in the sealing unit fixed to the stage, the portion may interfere with the extraction electrode. According to the above aspect, the portion projecting higher than the top surface of the stage is hardly formed because the position of the sealing unit can be lowered.

Preferably, the vacuum processing apparatus further includes: a urging member that urges the plate-shaped member in a direction in which the plate-shaped member is detached from the inner wall of the processing chamber; and a restricting member that restricts an angle formed by the plate-shaped member and the inner wall of the processing chamber such that the angle is not larger than a predetermined angle. When the angle formed by the plate member and the inner wall of the processing chamber is at the predetermined angle, the opening end of the penetration opening on the opposite side to the inner wall is located at the same level as that of the stage.

In this aspect, the plate-shaped member is urged in a direction in which the plate-shaped member is detached from the inner wall of the processing chamber by the urging member, so that the plate-shaped member automatically becomes an open state when the sealing unit is separated from the plate-shaped member (that is, when the stage starts to move from the load lock chamber to the processing chamber). When the plate-shaped member rotates by the predetermined angle, the plate-shaped member is restricted by the restricting member so as not to further rotate. The opening end of the plate-shaped member on the opposite side to the inner wall in the penetration opening is located at the same level as the stage while the plate-shaped member is being restricted by the restricting member. Thus, when moving from the processing chamber to the load lock chamber, the stage can pass through the penetration opening without being caught by the opening end.

Preferably, the vacuum processing apparatus further includes a moving mechanism that moves the stage. The moving mechanism includes: a base member coupled to the sealing unit; a first guide rail that guides the base member in the processing chamber; a connecting rod coupled to the base member at one end, the connecting rod being inserted in a hole made in a sidewall of the processing chamber, the other end being disposed outside the processing chamber; a movable plate coupled to the other end of the connecting rod; a second guide rail that guides the movable plate; and a bellows disposed between the movable plate and the sidewall, the bellows following displacement of the movable plate while airtightness of the processing chamber is maintained. The movable plate is larger than the opening of the communication unit on the processing chamber side when viewed from the load lock chamber side toward the processing chamber side.

It is supposed here that the sealing unit, the base member, the connecting rod, and the movable plate are considered as one member, and this member is referred to as a member of interest. When the stage is placed in the load lock chamber in the atmospheric state, magnitude of atmospheric force pushing the member of interest toward the processing chamber side with the plate-shaped member interposed between them is proportional to the area of the opening of the communication unit on the processing chamber side. On the other hand, magnitude of atmospheric force pushing the member of interest toward the load lock chamber side is proportional to the area of the movable plate (an area viewed along a horizontal direction). According to the configuration in which the movable plate is larger than the opening of the communication unit as viewed from the load lock chamber side toward the processing chamberside, even if driving force of the moving mechanism is lost while the stage is placed in the load lock chamber in the atmospheric state, the member of interest is pressed against the load lock chamber side, and the divided state of the load lock chamber and the processing chamber is maintained. That is, even if the driving force of the moving mechanism is lost due to an unexpected situation such as a power failure, the sealing of the processing chamber is assured so as not to be broken.

Advantageous Effects of Invention

Since the opening of the communication unit on the processing chamber side is sealed by the sealing unit fixed to the stage when the stage is in the load lock chamber, the load lock chamber and the processing chamber are automatically separated from each other when the object is transferred from the processing chamber to the load lock chamber. Thus, the time necessary for the exchange operation between the load lock chamber and the processing chamber can be shortened.

DESCRIPTION OF EMBODIMENTS

Hereinafter, preferred embodiments of the present invention will be described with reference to the drawings.

1. Vacuum Processing Apparatus According to Embodiment

Figure 1:
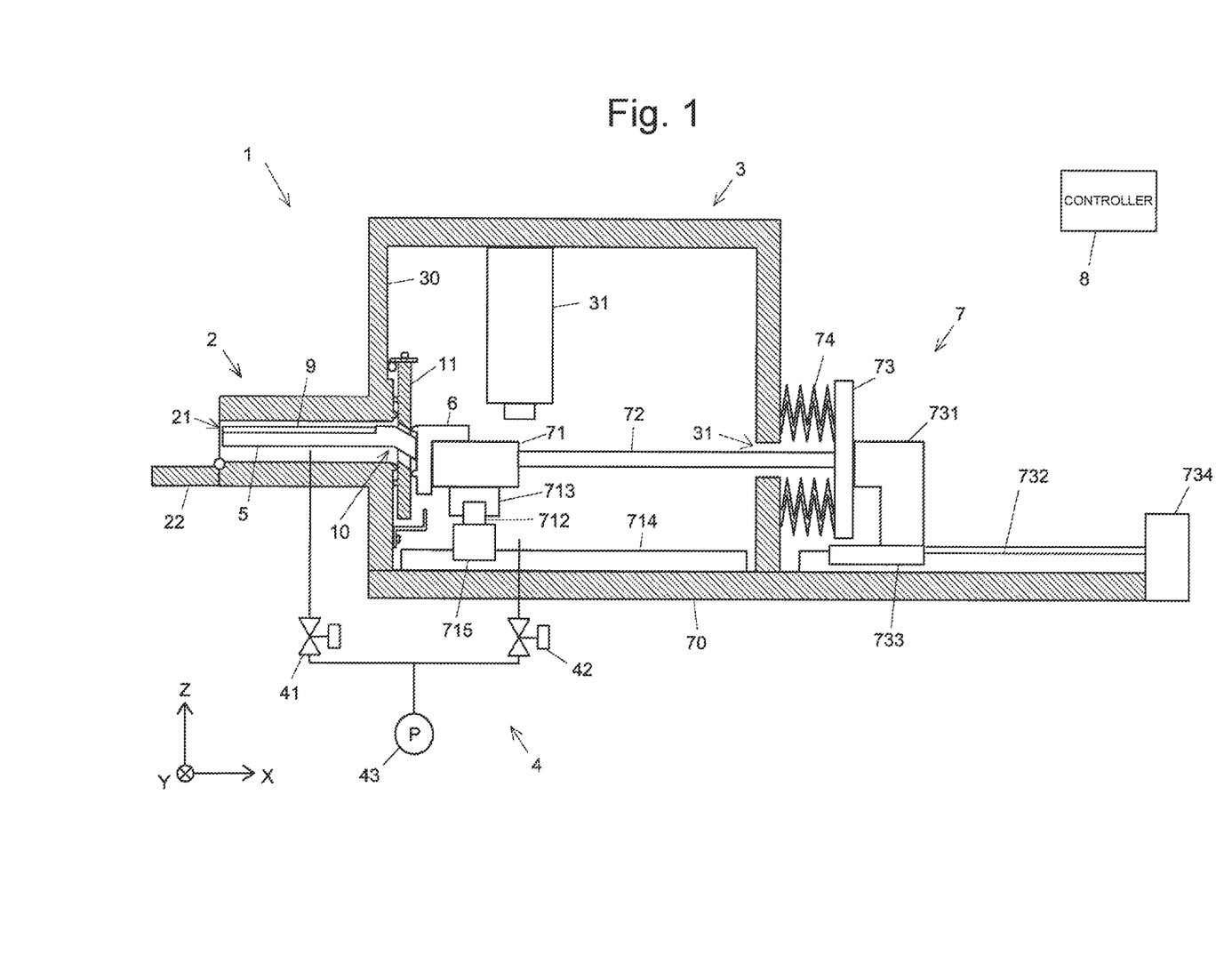
FIG. 1 is a longitudinal sectional view illustrating a part of a mass spectrometer, and is a view illustrating a state in which a stage is located on a load lock chamber side.
Figure 2:
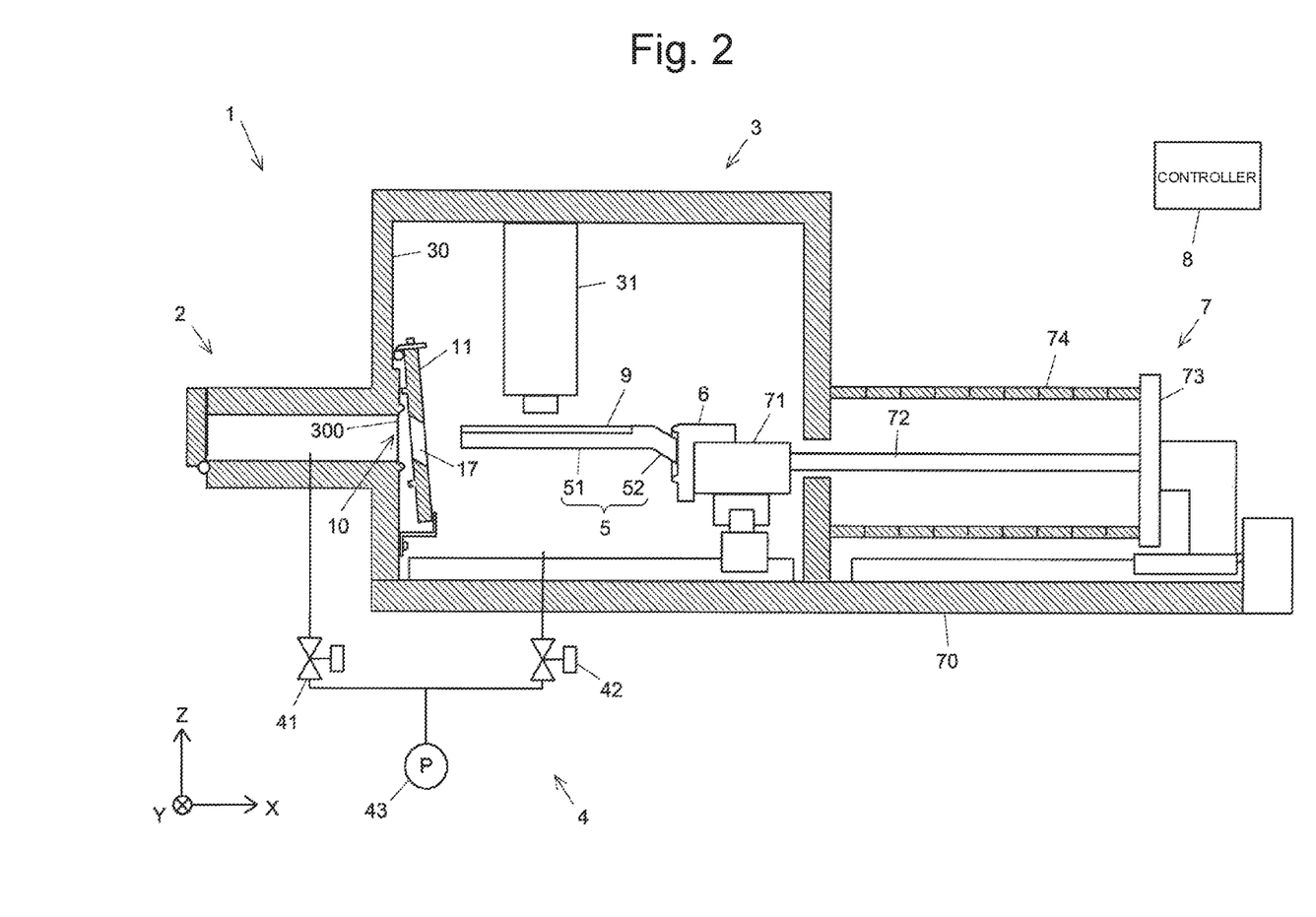
FIG. 2 is a longitudinal sectional view illustrating a part of the mass spectrometer, and is a view illustrating a state in which the stage is located on a processing chamber side.

FIGS. 1 and 2 are longitudinal sectional views illustrating a part of a mass spectrometer 1 that is an example of a vacuum processing apparatus. FIG. 1 illustrates a state in which a stage 5 is located on a side of a load lock chamber 2, and FIG. 2 illustrates a state in which the stage 5 is located on a side of a processing chamber 3.

The mass spectrometer 1 is a device that irradiates an object (sample 90 (see FIG. 4)) with a laser beam under vacuum to perform ionization, and separates and detects flying ions according to a mass-to-charge ratio. The sample 90 is held on a sample plate 9. Specifically, the sample plate 9 is a plate-shaped member, and a plurality of recesses 91 are formed on a top surface of the sample plate 9. The sample 90 is dropped onto each of the plurality of recesses 91, whereby the sample 90 is held on the sample plate 9 (see FIG. 4).

The mass spectrometer 1 includes the load lock chamber 2 in which the sample plate 9 is exchanged between the outside of the apparatus and the processing chamber 3, the processing chamber 3 in which a process is performed on the sample 90 held by the sample plate 9, and an evacuation system 4 that independently evacuates the load lock chamber 2 and the processing chamber 3. The load lock chamber 2 and the processing chamber 3 are connected to each other, and a communication unit 10 that communicates the load lock chamber 2 and the processing chamber 3 is formed between the load lock chamber 2 and the processing chamber 3. The mass spectrometer 1 also includes the stage 5 on which the sample plate 9 is placed, a sealing unit 6 fixed to the stage 5, and a moving mechanism 7 that moves the stage 5. The mass spectrometer 1 also includes a controller 8 that controls each unit of the mass spectrometer 1 to cause the unit to perform a series of processes on the sample plate 9.

<Load Lock Chamber 2>

As described above, the load lock chamber 2 is a chamber in which the sample plate 9 is exchanged between the outside of the apparatus and the processing chamber 3, and has a minimum size necessary for exchanging the sample plate 9. Specifically, the load lock chamber 2 is formed such that the internal volume of the load lock chamber 2 becomes the minimum size that can accommodate a placement portion 51 of the sample plate 9 in the stage 5. Hereinafter, the state in which the stage 5 is located on the side of the load lock chamber 2 means a state in which the entire placement portion 51 of the sample plate 9 is disposed in the load lock chamber 2.

The load lock chamber 2 includes an insertion port 21 of the sample plate 9 and a door 22 that opens and closes the insertion port 21. A leading end of the stage 5 reaches a vicinity of the insertion port 21 while the stage 5 is located on the side of the load lock chamber 2. At this point, an operator can insert the sample plate 9 from the insertion port 21, and places the sample plate 9 on the placement portion 51 of the stage 5.

The load lock chamber 2 is connected to a vacuum pump 43 through a pipe in which the valve 41 is inserted. When the communication unit 10 is closed while the door 22 is closed, the load lock chamber 2 becomes a sealed space. At this point, when the valve 41 is opened while the vacuum pump 43 is driven, the load lock chamber 2 is brought into a vacuum state.

<Processing Chamber 3>

A process, in which the sample 90 held on the sample plate 9 of the stage is ionized by irradiating the sample 90 with the laser beam from a laser beam source (not illustrated) and an ionized substance is extracted by an extraction electrode 31, is performed in the processing chamber 3 under vacuum. However, as described above, the sample 90 is held in each of the plurality of recesses 91 in the sample plate 9. In order to sequentially irradiate the sample 90 held in each recess 91 with the laser beam, the above process is performed while the moving mechanism 7 moves the stage 5 in the processing chamber 3 with respect to the laser beam source. The substance extracted by the extraction electrode 31 is accelerated, separated according to the mass-to-charge ratio, and detected (a configuration relating to the separation and the detection is not illustrated).

When the ionized substance is extracted by the extraction electrode 31, a pulsed high voltage of several kilovolts is applied to the extraction electrode 31 in order to form a preset electric field gradient between the extraction electrode 31 and the sample plate 9. It is necessary to increase the voltage applied to the extraction electrode 31. Enlargement of a power supply with increasing separation distance between the sample plate 9 and the extraction electrode 31, and improvement of a withstanding voltage of components relating to voltage supply, and the like are required when the large voltage is applied to the extraction electrode 31. Due to such circumstances, it is preferable that the extraction electrode 31 is located at a position very close to the sample plate 9 (preferably a position where the separation distance from the sample plate 9 is several millimeters). For this reason, in the mass spectrometer 1, the extraction electrode 31 is disposed such that a lower end of the extraction electrode 31 is located at a position separated by a sufficiently small distance (for example, 3 mm) from a horizontal plane through which the top surface of the sample plate 9 placed on the stage 5 passes.

The processing chamber 3 is connected to the vacuum pump 43 through a pipe in which a valve 42 is inserted. When the communication unit 10 is closed, the processing chamber 3 becomes the sealed space. At this point, when the valve 42 is opened while the vacuum pump 43 is driven, the processing chamber 3 becomes the vacuum state, and the above process can be performed. However, as will become clear later, the processing chamber 3 is maintained at a preset degree of vacuum during the successive process of a plurality of sample plates 9, but the processing chamber 3 is not evacuated each time the sample plate 9 is exchanged.

<Stage 5>

The stage 5 is a member on Which the sample plate 9 is placed. Specifically, the placement portion 51 that is a flat region where the sample plate 9 is placed is formed at one end (leading end) of the stage 5. The other end (base end) of the stage 5 is coupled to the moving mechanism 7 with the sealing unit 6 interposed between them, and the placement portion 51 becomes horizontal in this coupled state.

The base end of the stage 5 is fixed to the sealing unit 6, and an inclined portion 52 inclined obliquely downward toward the sealing unit 6 is formed in the base end. This corresponds to the fact that a penetration opening 17 of a plate-shaped member 11 (to be described later) is formed while inclined, and an inclination angle of the inclined portion 52 is identical to an inclination angle of the penetration opening 17.

<Moving Mechanism 7>

The moving mechanism 7 is a mechanism that moves the stage 5 in a horizontal plane specifically, in the X direction (in which the load lock chamber 2 and the processing chamber 3 are disposed) and a Y direction). The moving mechanism 7 is the mechanism that moves the stage 5 between the processing chamber 3 and the load lock chamber 2 through the communication unit 10, and is the mechanism that moves the stage 5 in the processing chamber 3 as described above (that is, moves the stage 5 relative to the laser beam source).

The moving mechanism 7 includes a base member 71 coupled to the sealing unit 6. The base member 71 is fixed on a linear block 713 that is disposed on a Y guide rail 712 laid in the Y direction in the processing chamber 3. The Y guide rail 712 is fixed on a linear block 715 that is disposed on an X guide rail (first guide rail) 714 laid in the X direction in the processing chamber 3. The X guide rail 714 and the Y guide rail 712 are laid so as to extend horizontally, and the X guide rail 714 and the Y guide rail 712 are assured such that the placement portion 51 of the stage 5 coupled to the base member 71 with the sealing unit 6 interposed between them moves within a horizontal plane.

The base member 71 is fixed to one end of a connecting rod 72. The connecting rod 72 is inserted in a hole 31 made in a sidewall of the processing chamber 3, and the other end of the connecting rod 72 is coupled to a movable plate 73 disposed outside the processing chamber 3. The movable plate 73 has a size lager than an opening 300 of the communication unit 10 on the side of the processing chamber 3 when viewed from the side of the load lock chamber 2 toward the side of the processing chamber 3.

A space between the movable plate 73 and the outer wall of the processing chamber 3 is sealed by a bellows 74. That is, one end of the bellows 74 is bonded to the outer wall of the processing chamber 3 while the other end is bonded to the movable plate 73, and the bellows 74 follows displacement of the movable plate 73 while airtightness of the processing chamber 3 is maintained.

A Y actuator 731 that moves the movable plate 73 along the Y direction is connected to the movable plate 73. The movable plate 73 and the Y actuator 731 are disposed on an X stage 733 mounted on an X guide rail (second guide rail) 732 laid in the X direction. An X actuator 734 that moves the X stage 733 along the X direction connected to the X stage 733. The Y actuator 731, the second guide rail 732, the X stage 733, and the X actuator 734 are disposed outside the processing chamber 3. However, the first guide rail 714 and the second guide rail 732 are preferably disposed on a common base 70 in order to easily assure mutual position accuracy. For example, a ball screw drive method, a linear motor drive method, or a belt drive method can be adopted as the X actuator 734 and the Y actuator 731.

2. Configuration Relating to Closing of Communication Unit 10

Figure 3:
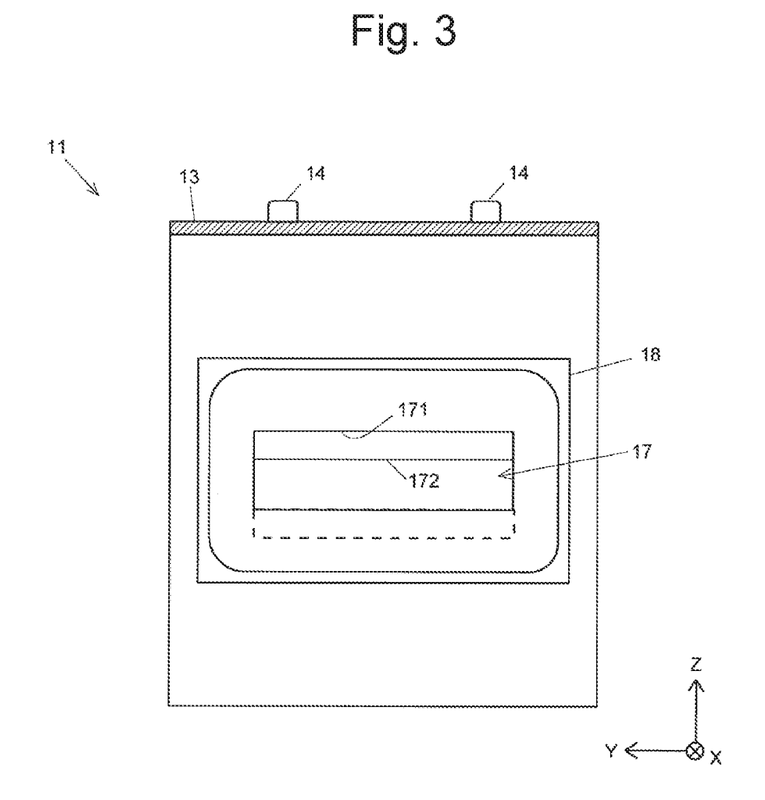
FIG. 3 is a view of a plate-shaped member when the plate-shaped member is viewed from a −X direction in FIG. 1.
Figure 4:
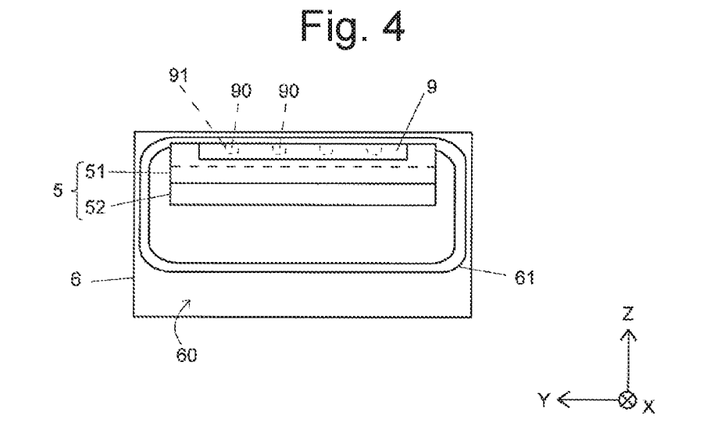
FIG. 4 is a view of the stage and a sealing unit when the stage and the sealing unit are viewed from the −X direction in FIG. 1.
Figure 5:
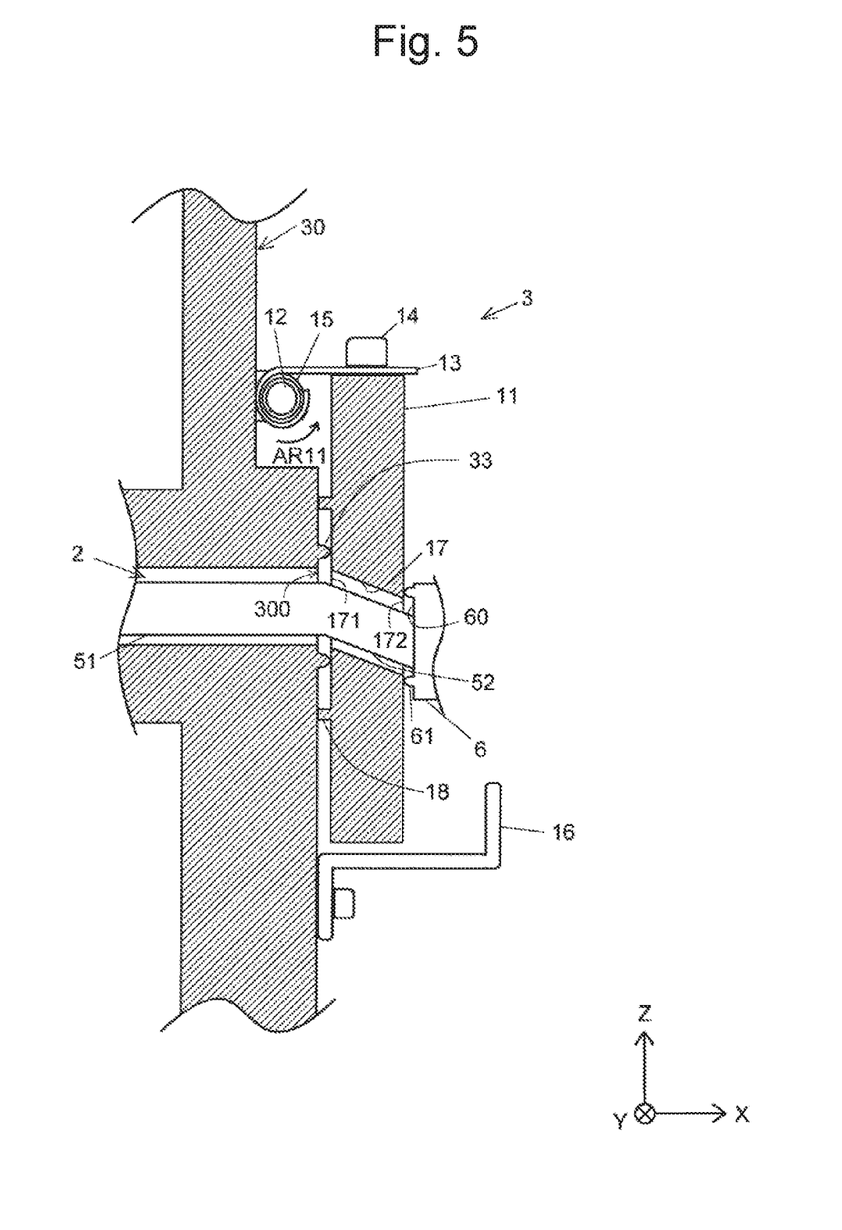
FIG. 5 is a main-part enlarged view illustrating a configuration relating to closing of a communication unit.
Figure 6:
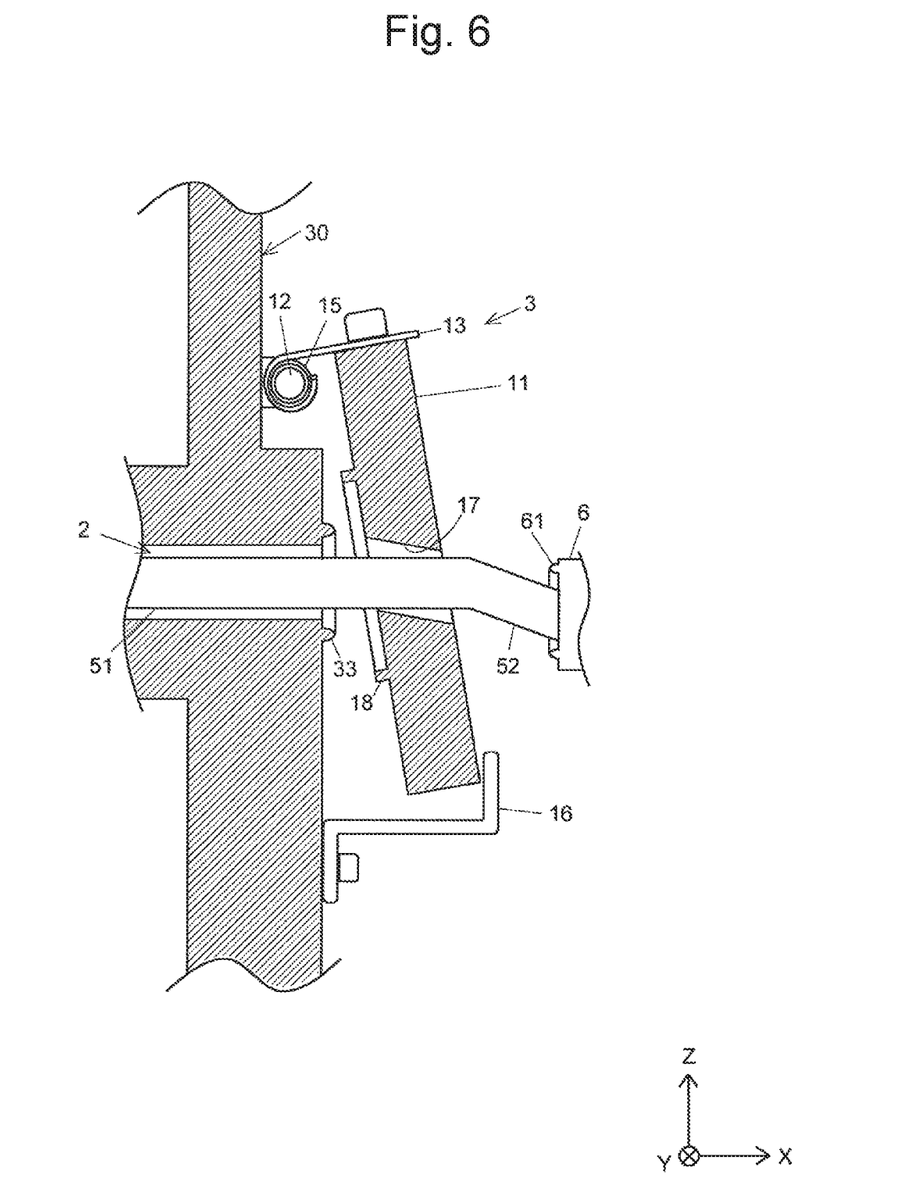
FIG. 6 is another main-part enlarged view illustrating the configuration relating to the closing of the communication unit.
Figure 7:
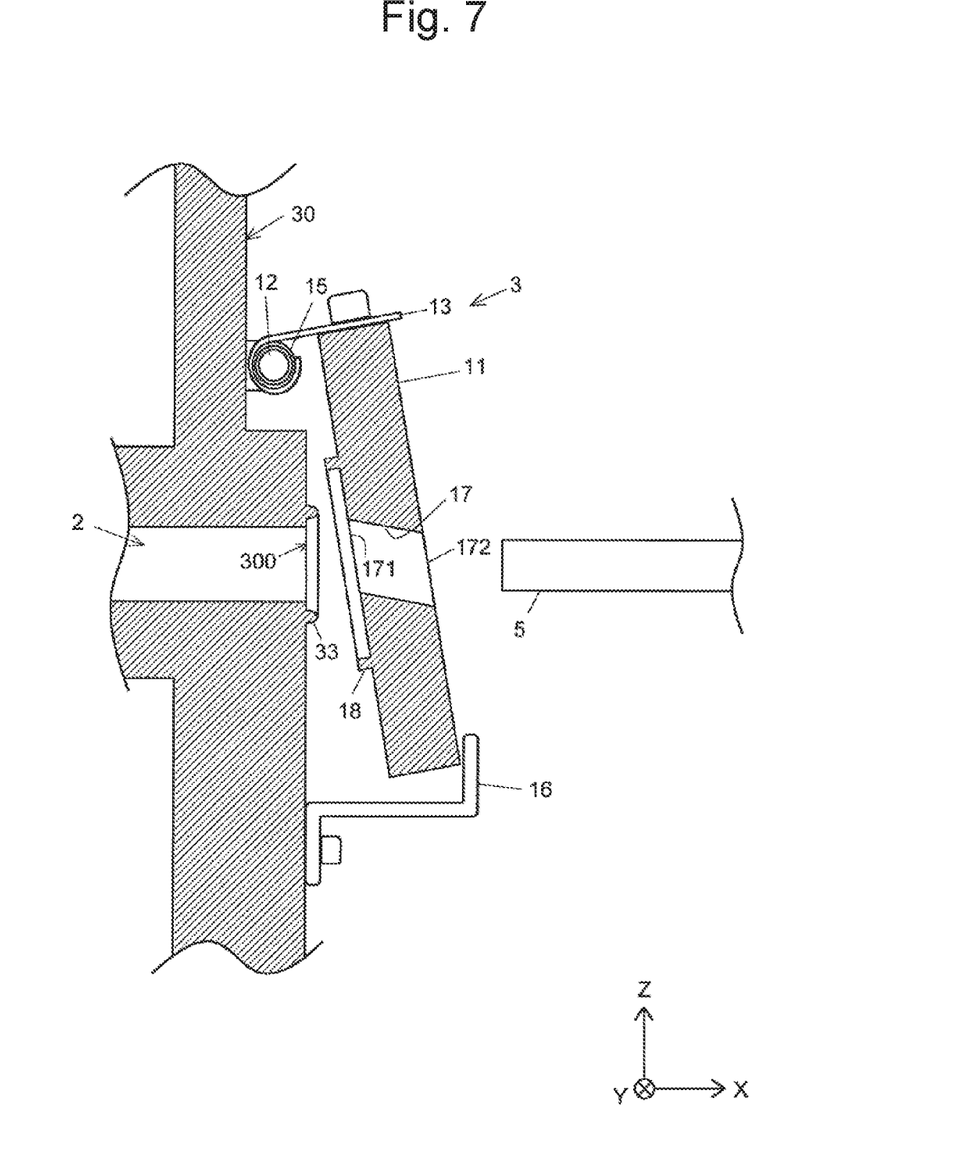
FIG. 7 is still another main-part enlarged view illustrating the configuration relating to the closing of the communication unit.

In the mass spectrometer 1, the communication unit 10 is closed when the stage 5 is disposed in the load lock chamber 2. The configuration relating to the closing of the communication unit 10 will be described with reference to FIGS. 3 to 7, in addition to FIGS. 1 and 2. FIG. 3 is a view of the plate-shaped member 11 when the plate-shaped member 11 is viewed from a −X direction in FIG. 1. FIG. 4 is a view of the stage 5 and a sealing unit 6 when the stage 5 and the sealing unit 6 are viewed from the −X direction in FIG. 1. FIGS. 5 to 7 are main-part enlarged views illustrating the configuration relating to the closing of the communication unit 10. FIG. 5 illustrates a state in which the communication unit 10 is closed while the stage 5 is located on the side of the load lock chamber 2. FIG. 6 illustrates a middle state in which the stage 5 is moved from the side of the load lock chamber 2 to the side of the processing chamber 3. FIG. 7 illustrates a state in which the stage 5 is located on the side of the processing chamber 3.

<Plate-Shaped Member 11>

The plate-shaped member 11 is a tabular member larger than an opening (that is, an opening of the communication unit 10 in an inner wall 30 of the processing chamber 3, hereinafter also simply referred to as "an opening") 300 of the communication unit 10 on the side of the processing chamber 3, and is provided such that a main surface of the plate-shaped member 11 covers a region around the opening 300 from the side of the processing chamber 3. Specifically, a horizontally extending turning shaft 12 is disposed on the inner wall 30 of the processing chamber 3 and above the opening 300. A hinge member 13 is rotatably disposed on the turning shaft 12, and an upper side of the plate-shaped member 11 is fixed to the hinge member 13 with a screw 14 or the like. Consequently, the plate-shaped member 11 is provided so as to be switchable between a closed state (the state in FIG. 5) in which the plate-shaped member 11 abuts on the inner wall 30 and an open state (the state in FIGS. 6 and 7) in which the plate-shaped member 11 is detached from the inner wall 30.

The hinge member 13 is what is called a spring hinge in which an urging member (specifically, for example, a torsion spring) 15 is incorporated. The plate-shaped member 11 is always urged in the direction in which the plate-shaped member 11 is separated from the inner wall 30 of the processing chamber 3 (that is, in an opening direction) by the urging member 15 (arrow AR11).

A restricting member 16, which restricts an angle formed by the plate-shaped member 11 and the inner wall 30 such that the angle is not larger than a predetermined angle, is provided on the inner wall 30 of the processing chamber 3 and below the opening 300. For example, the restricting member 16 is a member having an L-shape section. When the angle formed by the plate-shaped member 11 and the inner wall 30 of the processing chamber 3 reaches the predetermined angle, the restricting member 16 is caught by a lower portion of the plate-shaped member 11 such that the angle is not larger than the predetermined angle (the state in FIGS. 6 and 7). Specifically, the predetermined angle is an angle at which a second opening end 172 (to be described later) is located at the same level as the stage 5 (specifically, the level of the horizontal plane on which the stage 5 is moved) when the angle formed by the plate-shaped member 11 and the inner wall 30 of the processing chamber 3 is the predetermined angle.

The penetration opening 17 through which the stage 5 passes is formed in the plate-shaped member 11. The penetration opening 17 is formed obliquely downwardly as going away from the inner wall 30 of the processing chamber 3, and the opening end (second opening end) 172 opened to a surface on the opposite side to the inner wall 30 is formed at a position lower than an opening end (first opening end) 171 opened to a surface opposed to the inner wall 30. However, the first opening end 171 is formed at a position corresponding to the opening 300 (specifically, a position overlapping the opening 300) when the plate-shaped member 11 is in the closed state. Thus, the second opening end 172 is disposed at a position lower than the opening 300. As described above, the inclined portion 52 inclined at the same angle as the penetration opening 17 is formed at the base end of the stage 5, and the inclined portion 52 is disposed inside the penetration opening 17 while the stage 5 is located on the side of the load lock chamber 2 (the state in FIG. 5).

In the embodiment, the openings 300 of the communication unit 10 and the open ends (the first opening end 171 and the second opening end 172) of the penetration opening 17 have substantially the same shape and substantially the same size.

A seal unit (first seal 18 that seals a gap between the plate-shaped member 11 and the inner wall 30 is formed in the plate-shaped member 11. Specifically, the first seal unit 18 is a bank-shaped projection surrounding the first opening end 171, and an entire circumference of the first seal unit 18 abuts on the inner wall 30 in a close contact state while collectively surrounding the opening 300 and the first opening end 171 when the plate-shaped member 11 is in the closed state.

In the embodiment, a seal unit (second seal unit) 33 that seals a gap between the plate-shaped member 11 and the inner wall 30 is also formed in the inner wall 30. Specifically, the second seal unit 33 is a bank-like projection surrounding the opening 300, and an entire circumference of the second seal unit 33 abuts on the plate-shaped member 11 in the close contact state while collectively surrounding the opening 300 and the first opening end 171 when the plate-shaped member 11 is in the closed state. The first seal unit 18 and the second seal unit 33 are formed at positions in which the first seal unit 18 and the second seal unit 33 do not interfere with each other, and the first seal unit 18 and the second seal unit 33 are formed at the same level. However, one of the first seal unit 18 and the second seal unit 33 may be omitted.

<Sealing Unit 6>

As described above, the sealing unit 6 is fixed to one end (base end) of the stage 5. A surface (hereinafter also referred to as "a sealing surface") 60 of the sealing unit 6 to which the base end of the stage 5 is attached has a size larger than the second opening end 172 of the penetration opening 17 formed in the plate-shaped member 11, and the sealing unit 6 does not enter the penetration opening 17. Thus, the sealing unit 6 abuts on the plate-shaped member 11 at a certain point of time when the stage 5 is moved to the side of the load lock chamber 2, the sealing unit 6 rotates the plate-shaped member 11 against the urging force of the urging member 15 (specifically, the spring force of the spring hinge) when the stage 5 is further moved, and finally the sealing unit 6 presses the plate-shaped member 11 against the inner wall 30 of the processing chamber 3 (that is, the plate-shaped member 11 is brought into the closed state).

A seal unit (third seal unit) 61 that seals a gap between the plate-shaped member 11 and the sealing surface 60 is formed in the sealing surface 60. Specifically, the third seal unit 61 is a bank-shaped projection that can surround the second opening end 172, and the entire circumference of the third seal unit 61 abuts on the plate-shaped member 11 in the close contact state while surrounding the second opening end 172 when the stage 5 is disposed on the side of the load lock chamber 2.

As described above, the inclined portion 52 inclined at the same angle as the penetration opening 17 of the plate-shaped member 11 is formed at the base end of the stage 5, and the position of the sealing unit 6 is lower than the top surface of the stage 5 by the inclination of the inclined portion 52. Consequently, the sealing unit 6 is assured so as not to interfere with the extraction electrode 31.

3. Operation of Mass Spectrometer 1

Operation of the mass spectrometer 1 will be described below with reference to FIGS. 1 to 7. A series of operation described below is performed under the control of the controller 8.

In the state in which the mass spectrometer 1 is ready to receive the new sample plate 9, the door 22 is opened while the stage 5 is disposed on the side of the load lock chamber 2 (the state in FIG. 1). When the stage 5 is disposed in the load lock chamber 2, the inclined portion 52 of the stage 5 is disposed in the penetration opening 17, the sealing unit 6 abuts on the plate-shaped member 11, and the plate-shaped member 11 is in the closed state. At this point, the gap between the plate-shaped member 11 and the inner wall 30 of the processing chamber 3 is sealed by the first seal unit 18 and the second seal unit 33, and the gap between the plate-shaped member 11 and the sealing surface 60 is sealed by the third seal unit 61. Consequently, the opening 300 of the communication unit 10 is closed. Thus, the vacuum in the processing chamber 3 will not be broken even if the door 22 is opened.

When the door 22 is opened, the operator inserts the sample plate 9 on which the sample 90 is held from the insertion port 21, and places the sample plate 9 on the placement portion 51 of the stage 5. When a sensor (not illustrated) or the like detects that the new sample plate 9 is placed on the stage 5, the door 22 is closed, the insertion port 21 is closed, and the load lock chamber 2 becomes the sealed space. Then, the valve 41 is opened while the vacuum pump 43 is driven. Consequently, the load lock chamber 2 is depressurized.

When the load lock chamber 2 becomes a preset vacuum state, the moving mechanism 7 starts to move the stage 5 on which the sample plate 9 is placed from the side of the load lock chamber 2 to the side of the processing chamber 3. When the stage 5 starts to move, the plate-shaped member 11 that is in the closed state by the abutment of the sealing unit 6 is rotated by the urging force of the urging member 15 to separate from the inner wall 30 of the processing chamber 3. When the angle formed by the plate-shaped member 11 and the inner wall 30 reaches the predetermined angle, the plate-shaped member 11 is caught by the restricting member 16, and the rotation of the plate-shaped member 11 is stopped. Then, the stage 5 is further moved to the side of the processing chamber 3 and the sample plate 9 comes to a preset position in the processing chamber 3. At this point, the process of the sample plate 9 is started. A content of the process performed in the processing chamber 3 is as described above.

When the process of the sample plate 9 is completed, the moving mechanism 7 starts to move the stage 5 on which the sample plate 9 is placed from the side of the processing chamber 3 to the side of the load lock chamber 2. The leading end of the stage 5 sequentially passes through the penetration opening 17 of the plate-shaped member 11 and the communication unit 10, and enters the load lock chamber 2. As described above, a posture of the plate-shaped member 11 is restricted by the restricting member 16 such that the second opening end 172 comes to the level at which the stage 5 is moved. Thus, the stage 5 can pass through the penetration opening 17 without being caught by the second opening end 172.

The sealing unit 6 abuts on the plate-shaped member 11 when the stage 5 is moved by a certain distance. When the stage 5 is further moved, the plate-shaped member 11 is pushed by the sealing unit 6 to rotate against the urging force of the urging member 15. When the stage 5 is completely disposed on the side of the load lock chamber 2, the plate-shaped member 11 abuts on the inner wall 30 of the processing chamber 3 to become the closed state. As described above, at this point, the opening 300 is closed.

After the stage 5 is disposed on the side of the load lock chamber 2, the vacuum in the load lock chamber 2 is broken and the door 22 is opened. As described above, when the stage 5 is located on the side of the load lock chamber 2, the opening 300 is closed, so that the vacuum in the processing chamber 3 will not be broken even if the door 22 is opened. When the operator takes out the sample plate 9 through the insertion port 21, the mass spectrometer 1 returns to the state in which the mass spectrometer 1 can receive the new sample plate 9.

4. When Power is Lost

Figure 8:
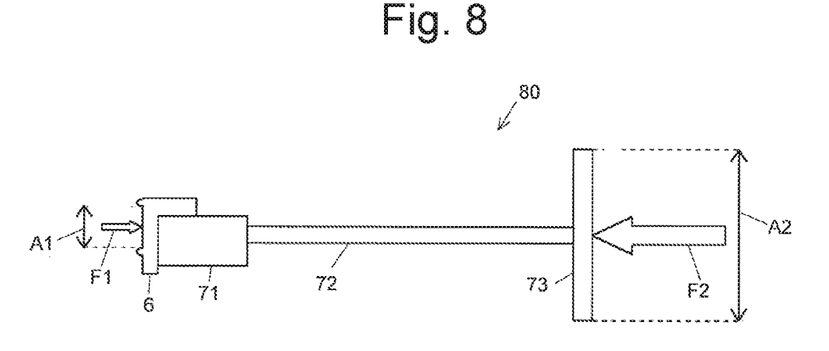
FIG. 8 is a view illustrating atmospheric force applied to a member of interest.

The case that driving force of the moving mechanism 7 is lost due to an unexpected situation such as a power failure while the stage 5 is disposed in the load lock chamber 2 in an atmospheric state in the mass spectrometer 1 will be described with reference to FIGS. 1 and 8. In the following description, the sealing unit 6, the base member 71, the connecting rod 72, and the movable plate 73 are regarded as one member, and this member is referred to as "a member of interest 80". FIG. 8 is a view illustrating atmospheric force applied to the member of interest 80.

It is assumed that the load lock chamber 2 is in an atmospheric state, that the processing chamber 3 is in a vacuum state, and that the stage 5 is disposed on the side of the load lock chamber 2 (the state in FIG. 1). At this point, magnitude of atmospheric force F1 pushing the member of interest 80 toward the side of the processing chamber 3 with the plate-shaped member 11 interposed between them is proportional to an area (an area viewed from side of the load lock chamber 2 toward the side of the processing chamber 3) A1 of the opening 300 of the communication unit 10 on the side of the processing chamber 3. On the other hand, magnitude of atmospheric force F2 pushing the member of interest 80 toward the side of the load lock chamber 2 is proportional to an area (an area viewed from side of the load lock chamber 2 toward the side of the processing chamber 3) A2 of the movable plate 73.

At this point, the movable plate 73 is formed such that the area A2 of the movable plate 73 is larger than the area A1 of the opening 300. Thus, the magnitude of the atmospheric force F2 pushing the member of interest 80 toward the side of the load lock chamber 2 is larger than the atmospheric force F1 pushing the member of interest 80 toward the side of the processing chamber 3. For this reason, even if the driving force of the moving mechanism 7 is lost, the member of interest 80 is maintained in the state in which the member of interest 80 is pressed against the side of the load lock chamber 2 by the atmospheric force. That is, the state in which the load lock chamber and the processing chamber 3 are separated is maintained. As described above, in the mass spectrometer 1, even if the driving force of the moving mechanism 7 is lost due to the unexpected situation such as the power failure when the load lock chamber 2 is in the atmospheric state, the sealing of the processing chamber 3 is assured not so as not to be broken.

5. Other Embodiments

In the above embodiment, a seal unit that seals the gap between the plate-shaped member 11 and the sealing unit 6 may be provided in the surface of the plate-shaped member 11 on the side of the sealing unit 6. Specifically, the seal unit is a bank-shaped projection surrounding the second opening end 172, and an entire circumference of the seal unit abuts on the sealing surface 60 in the close contact state while surrounding the second opening end 172 when the sealing unit 6 abuts on the plate-shaped member 11. In the case that the seal unit is provided, the third seal unit 61 may be omitted.

Figure 9:
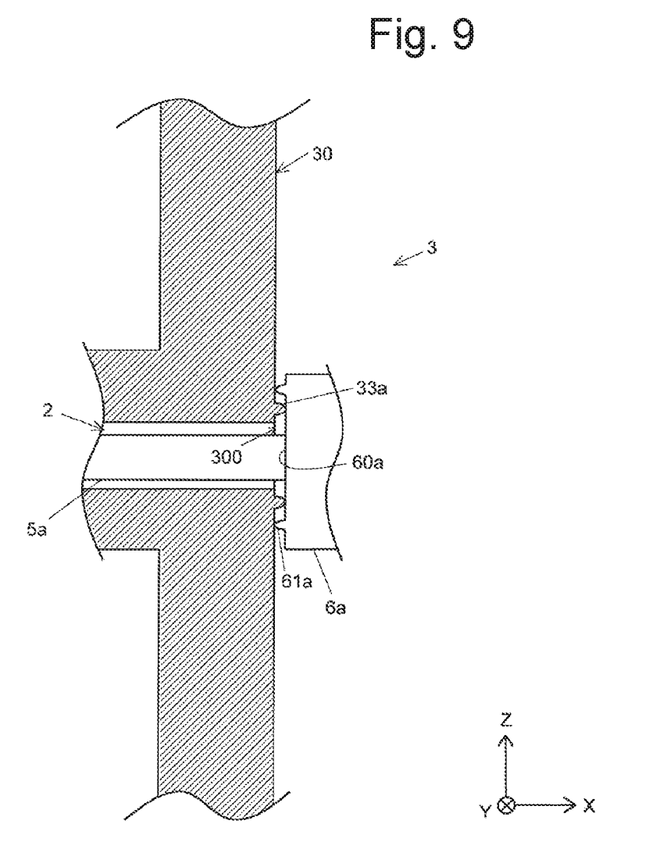
FIG. 9 is a main-part enlarged view illustrating a configuration relating to closing of a communication unit according to another embodiment.

In the above embodiment, the plate-shaped member 11 is not necessarily provided. FIG. 9 illustrates a configuration example in the case that the plate-shaped member 11 is not provided. In this case, the stage 5a is formed by a tabular member as a whole, and the inclined portion is not formed. A sealing surface 60a of the sealing unit 6a has a size larger than the opening 300 of the communication unit 10, and the sealing unit 6a does not enter the communication unit 10. A seal unit (fourth seal unit) 61a that seals a gap between the sealing surface 60a and the inner wall 30 of the processing chamber 3 is formed in the sealing surface 60a. Specifically, the fourth seal unit 61a is a bank-shaped projection that can surround the opening 300, and the entire circumference of the fourth seal unit 61a abuts on the inner wall 30 in the close contact state while surrounding the opening 300 when the stage 5a is disposed on the side of the load lock chamber 2.

Preferably, a seal unit (a fifth seal unit) 33a that seals a gap between the inner wall 30 and the sealing unit 6a is also formed in the inner wall 30. Specifically, the fifth seal unit 33a is a bank-like projection that surrounds the opening 300, and the entire circumference of the fifth seal unit 33a abuts on the sealing surface 60a in the close contact state while surrounding the opening 300 when the stage 5a is disposed in the load lock chamber 2. The fourth seal unit 61a and the fifth seal unit 33a are formed at positions in which the fourth seal unit 61a and the fifth seal unit 33a do not interfere with each other, and the fourth seal unit 61a and the fifth seal unit 33a are formed at the same level. However, one of the fourth seal unit 61a and the fifth seal unit 33a may be omitted.

In the above embodiment, the urging member 15 that urges the plate-shaped member 11 in the opening direction is provided in the plate-shaped member 11, and the restricting member 16 that restricts the posture of the plate-shaped member 11 is provided. However, the urging member 15 and the restricting member 16 are not necessarily provided. For example, an opening and closing switch that opens and closes the plate-shaped member 11 may be provided, and the controller 8 may control the opening and closing switch.

In the above embodiment, the present invention is applied to the mass spectrometer. However, the present invention can also be applied to various vacuum processing apparatuses other than the mass spectrometer.

REFERENCE SIGNS LIST

1 . . . Mass spectrometer
2 . . . Load lock chamber
3 . . . Processing chamber
4 . . . Evacuation system
5 . . . Stage
6 . . . Sealing unit
7 . . . Moving mechanism
8 . . . Controller
9 . . . Sample plate
10 . . . Communication unit
11 . . . Plate-shaped member
12 . . . Turning shaft
13 . . . Hinge member
15 . . . Urging member
16 . . . Restricting member
17 . . . Penetration opening
18 . . . First seal unit
33 . . . Second seal unit
51 . . . Placement portion
52 . . . Inclined portion
60 . . . Sealing surface
61 . . . Third seal unit
71 . . . Base member
72 . . . Connecting rod
73 . . . Movable plate
74 . . . Bellows
171 . . . First opening end of the plate-shaped member
172 . . . Second opening end of the plate-shaped member
300 . . . Opening of the communication unit

The invention claimed is:

1. A vacuum processing apparatus comprising:
   a processing chamber that can bring an inside of the processing chamber into a vacuum state;
   a load lock chamber that is coupled to the processing chamber and that is switchable between an atmospheric state and the vacuum state;
   a communication unit configured to communicate the processing chamber with the load lock chamber;
   a stage on which a processing object is placed, the stage being movable between the processing chamber and the load lock chamber through the communication unit; and
   a sealing unit fixed to the stage, the sealing unit being larger than an opening of the communication unit on a processing chamber side;
   a plate-shaped member rotatably provided on a horizontal axis placed above the opening of the communication unit on the processing chamber side in an inner wall of the processing chamber, the plate-shaped member being switchable between a closed state in which the plate-shaped member abuts on the inner wall and an opened state in which the plate-shaped member is detached from the inner wall; and
   a penetration opening formed in the plate-shaped member to allow the stage to pass, wherein:
   an opening end of the penetration opening on the inner wall side is formed at a position corresponding to the opening of the communication unit on the processing chamber side when the plate-shaped member is in the closed state, while the penetration opening is inclined obliquely downward as the penetration opening goes away from the inner wall,
   an inclined portion inclined obliquely downward at an angle equal to that of the penetration opening is formed at an end of the stage on a side on which the sealing unit is fixed as it approaches the sealing unit,
   the sealing unit is larger than an opening end of the penetration opening on a side opposite to the inner wall, and
   in a state in which the stage is located on a load lock chamber side, the inclined portion of the stage is disposed inside the penetration opening, and the sealing unit abuts on the plate-shaped member to bring the plate-shaped member into the closed state.

2. The vacuum processing apparatus according to claim 1, further comprising:
an urging member that urges the plate-shaped member in a direction in which the plate-shaped member is detached from the inner wall of the processing chamber; and
a restricting member that restricts an angle formed by the plate-shaped member and the inner wall of the processing chamber such that the angle is not larger than a predetermined angle, wherein
when the angle formed by the plate-shaped member and the inner wall of the processing chamber is at the predetermined angle, the opening end of the penetration opening on the opposite side to the inner wall is located at the same level as that of the stage.

3. The vacuum processing apparatus according to claim 1, further comprising a moving mechanism that moves the stage, wherein:
the moving mechanism includes:
a base member coupled to the sealing unit;
a first guide rail that guides the base member in the processing chamber;
a connecting rod coupled to the base member at one end, the connecting rod being inserted in a hole made in a sidewall of the processing chamber, the other end being disposed outside the processing chamber;
a movable plate coupled to the other end of the connecting rod;
a second guide rail that guides the movable plate; and
a bellows disposed between the movable plate and the sidewall, the bellows following displacement of the movable plate while airtightness of the processing chamber is maintained, and
the movable plate is larger than the opening of the communication unit on the processing chamber side when viewed from the load lock chamber side toward the processing chamber side.

4. The vacuum processing apparatus according to claim 2, further comprising a moving mechanism that moves the stage, wherein:
the moving mechanism includes:
a base member coupled to the sealing unit;
a first guide rail that guides the base member in the processing chamber;
a connecting rod coupled to the base member at one end, the connecting rod being inserted in a hole made in a sidewall of the processing chamber, the other end being disposed outside the processing chamber;
a movable plate coupled to the other end of the connecting rod;
a second guide rail that guides the movable plate; and
a bellows disposed between the movable plate and the sidewall, the bellows following displacement of the movable plate while airtightness of the processing chamber is maintained, and
the movable plate is larger than the opening of the communication unit on the processing chamber side when viewed from the load lock chamber side toward the processing chamber side.

5. A mass spectrometer comprising:
a processing chamber that can bring an inside of the processing chamber into a vacuum state;
a load lock chamber that is coupled to the processing chamber and that is switchable between an atmospheric state and the vacuum state;
a communication unit configured to communicate the processing chamber with the load lock chamber;
a stage on which a processing object is placed, the stage being movable between the processing chamber and the load lock chamber through the communication unit; and
a sealing unit fixed to the stage, the sealing unit being larger than an opening of the communication unit on a processing chamber side;
a plate-shaped member rotatably provided on a horizontal axis placed above the opening of the communication unit on the processing chamber side in an inner wall of the processing chamber, the plate-shaped member being switchable between a closed state in which the plate-shaped member abuts on the inner wall and an opened state in which the plate-shaped member is detached from the inner wall; and
a penetration opening formed in the plate-shaped member to allow the stage to pass, wherein:
an opening end of the penetration opening on the inner wall side is formed at a position corresponding to the opening of the communication unit on the processing chamber side when the plate-shaped member is in the closed state, while the penetration opening is inclined obliquely downward as the penetration opening goes away from the inner wall,
an inclined portion inclined obliquely downward at an angle equal to that of the penetration opening is formed at an end of the stage on a side on which the sealing unit is fixed as it approaches the sealing unit,
the sealing unit is larger than an opening end of the penetration opening on a side opposite to the inner wall, and
in a state in which the stage is located on a load lock chamber side, the inclined portion of the stage is disposed inside the penetration opening, and the sealing unit abuts on the plate-shaped member to bring the plate-shaped member into the closed state.

* * * * *